United States Patent [19]

Söderling

[11] Patent Number: 4,911,025
[45] Date of Patent: Mar. 27, 1990

[54] METHOD AND APPARATUS FOR PREPARING A SUSPENSION FOR MEASUREMENT

[75] Inventor: Peter Söderling, Tyresö, Sweden

[73] Assignee: S T F I, Stockholm, Sweden

[21] Appl. No.: 293,834

[22] Filed: Jan. 5, 1989

[51] Int. Cl.⁴ .............................................. G01N 1/00
[52] U.S. Cl. ...................................... 73/863; 356/436
[58] Field of Search ....................... 73/863, 865.3, 866,
73/865.5, 53, 61.4, 64.1, 63, 863; 324/71.4;
250/343; 356/436, 440, 441, 442

[56] References Cited

U.S. PATENT DOCUMENTS 3,472,371 10/1969 Ayerst et al. ................... 324/71.4 X Primary Examiner—Jerry W. Myracle
Attorney, Agent, or Firm—Fleit, Jacobson, Cohn, Price, Holman & Stern

[57] ABSTRACT

Method and apparatus for preparing a suspension for sample taking in a measurement section formed as a gap. The suspension provided with energy in a gap (10) immediately preceding the measurement section (11), which is enabled by the gap (10) being formed between a part (9) of a rotational body (4) and a part (5) surrounding it. These parts (9,5) are movable in relation to each other.

10 Claims, 1 Drawing Sheet

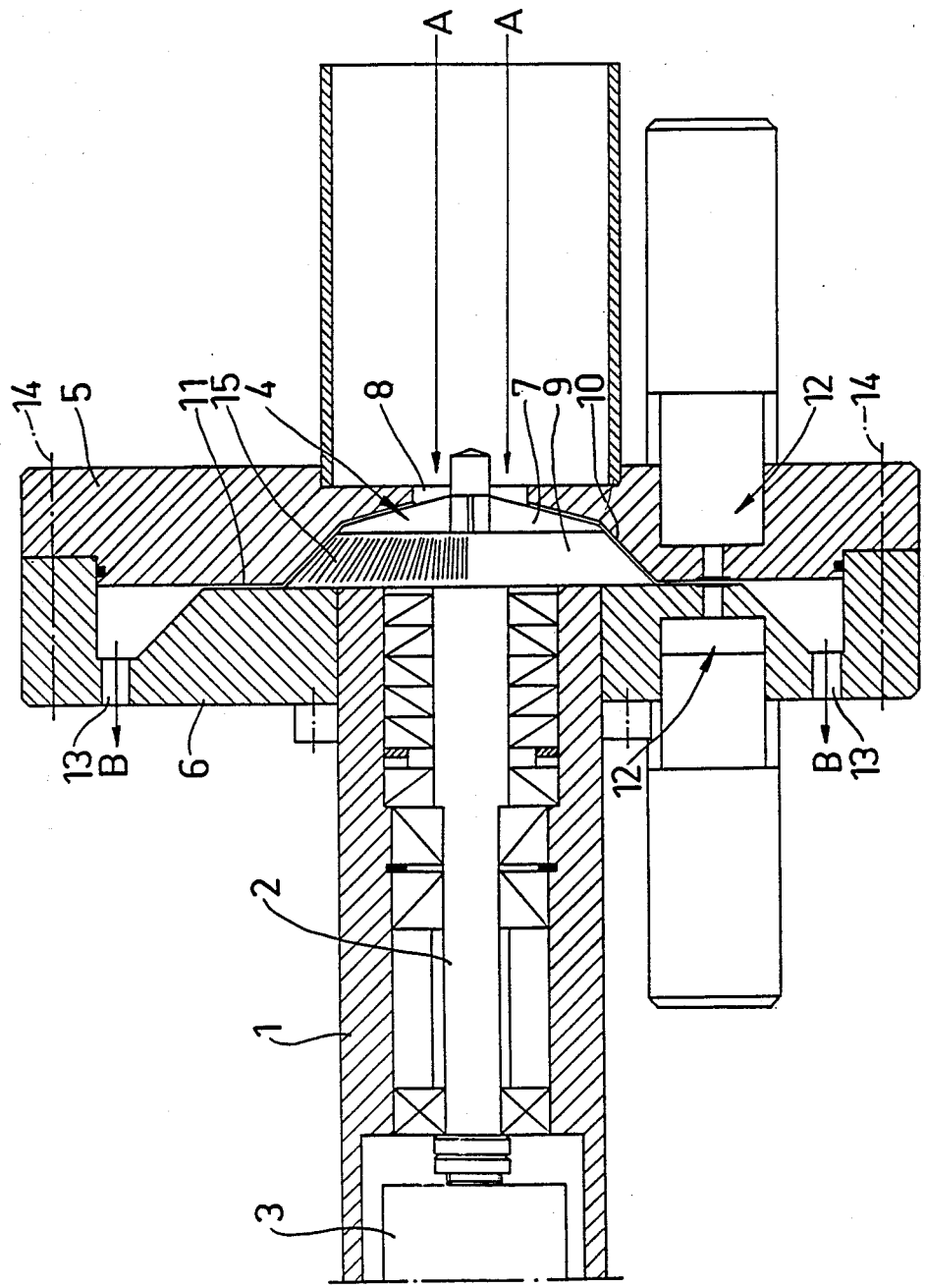

METHOD AND APPARATUS FOR PREPARING A SUSPENSION FOR MEASUREMENT

The present invention relates to a method and apparatus for preparing a suspension for sample taking in a measurement section formed as a gap.

In handling suspensions, there is a need of continuously checking the composition of a suspension, e.g. measuring size distribution in it, separating different kinds of particles or measuring the concentration of one kind of particle. Conventionally, in the technique in question here, an optical method ordinarily with the aid of photocells is used to carry out this checking, monitoring or measurement of the suspension. From the laboratory aspect, there are no substantial problems in such measurement, even in the case where the particles flocculate easily, e.g. in suspensions containing artificial or natural fibres. The problems occur in the intermittent or continuous measurement of a suspension directly in the industrial process, e.g. paper manufacturing. In these cases there is a pressing requirement of being able to measure the fibre concentration in such as papermaking stock. For this purpose it is at present necessary to process and measure samples of the suspension taken intermittently from the process. Measurement difficulties increase with dense or concentrated suspensions, and in such cases it is very often necessary to dilute the suspension before measurement. The measurement process is at present distinguished by complicated apparatus, which even so does not permit taking measurements directly in the process.

It is possible with the aid of the present invention readily to analyse, either intermittently or continuously, the suspension being treated in the process at the place and time required, thus to obtain a picture of the appearance of the suspension at that moment. For this purpose the invention has been given the distinguishing features disclosed in the claims.

The invention will now be described in the form of an example, and with reference to the drawing, schematically illustrating in section an embodiment of the apparatus in accordance with the invention.

In the FIGURE, the numeral 1 denotes a casing, carrying via bearings a shaft 2 driven by a motor 3. On the end of the shaft remote from the motor there is disposed an impeller 4 which, when driving by the motor, rotates in a housing formed in two parts 5 and 6. Further to the shaft bearings in the casing 1, the shaft is also sealed by suitably arranged seals, although neither seals or bearings will be dealt with here, since they are included in the known state of the art.

The impeller 4 is provided with blades 7 on its side facing towards an inlet 8. The impeller 4 also has a peripheral part 9 formed as the curved surface of a trucated cone. Together with the housing part 5 this peripheral part 9 forms a narrow gap 10. Similarly, when the parts have been assembled with the aid of screws or the like, indicated by the numeral 14, a second gap 11 is formed. The gap 11 is the measurement gap of the apparatus, and can have a width of 1 mm for example. It will be understood that it is in this measurement gap that measurement of the suspension is performed. An optical measurement means is illustrated in the FIGURE, and includes a light source and photocell, generally denoted by 12.

In order to measure suspensions of different kinds, particularly in the case where the suspension particles tend to flocculate, e.g in artificial or natural fibre suspensions, it is necessary to disintegrate the flocculations and distribute the fibres as uniformly as possible in the suspension, if reliable measurement of desired parameters is to be possible. However, it is not sufficient with this disintegration and uniform distribution; measurement must take place before flocculation reoccurs, which can happen very rapidly, particularly with heavy concentrations. The consequence of this has been that it has so far not been possible to measure the suspension directly in a process, e.g. that of producing paper pulp, and samples have had to be taken from the process for preparation, dilution etc.

By the present invention it has become possible also to measure concentrated suspensions taken directly from the process, e.g. by the suspension being drawn off via a shunt connection. Connection of the apparatus into the process is not discussed in more detail other than that a fibre suspension flows through the inlet 8 in the direction of the arrows A in the FIGURE. The impeller 4 with its blades 7 urges the suspension through the gap 10. In this gap the suspension has a relatively high pressure and the fibres are subjected to beating and slushing, which takes places immediately prior to the suspension reaching the measurement gap 11. In the latter there is thus a homogeneous suspension in which the fibres are distributed optimally. A very good measurement result is thus obtained. For the apparatus to function well, the gap between the peripheral part of the wheel 4 and the housing part 5 should be narrower than the actual measurement gap 11. The suspension leaves the housing 5,6 via peripherally distributed outlets 13, as indicated by the arrows B.

The peripheral part of the impeller 4 can be smooth, or it can be provided with a plurality of fine flutes or ridges, as indicated on one half of the impeller and denoted 15.

A further supply of energy to the suspension for disintegrating flocculation is also achieved by the measurement gap 11 forming an angle to the other gap 10 between the housing part 5 and impeller 4.

The measuring methods themselves as such do not form any part of this invention, and measurement may concern such as size distribution of particles, separation of different kinds of particles, concentration of one kind of particle, photographing of particles etc. It will also be understood that several measurement means can be distributed round the housing the measurement gap 11, for registering different parameters, if so desired. However, for the sake of simplicity only one measurement means has been depicted on the drawing.

I claim:

1. Method of preparing a suspension for sample taking in a measurement section, which measurement section is in the form of a gap defined between a pair of surfaces, characterized in that the suspension is supplied with energy in a gap immediately preceding the measurement gap.

2. Method as claimed in claim 1, characterised in that energy is supplied in a gap which has a width less than that of the measurement section 3. Method as claimed in claim 1, characterised in that energy is supplied by the suspension being subjected to pressure and by the defining surfaces of the gap being caused to move relative to each other.

4. Apparatus for carrying out the method preparing a suspension for sample taking in a measuring section which measurement section is in the form of a gap defined between a pair of surfaces, characterized in that immediately preceding the measurement gap there is arranged a gap, which is formed between a part of a rotational body and a part surrounding the body, said parts being movable in relation to each other.

5. Apparatus as claimed in claim 4, characterised in that the gap between the parts has a width less than that of the measurement section.

6. Apparatus as claimed in claim 5, characterised in that the rotation body is implemented as an impeller with the part of the rotational body forming one side of the gap arranged at the peripheral outlet edge of the impeller.

7. Apparatus as claimed in claim 5, characterised in that the width of the measuring section gap is about one 1 mm.

8. Apparatus as claimed in claim 4, characterised in that the part of the rotational body forming one side of the gap, is formed with flutes or ridges.

9. Apparatus as claimed claim 4, characterised in that the gap of the measurement section together with the gap preceding it mutually form an angle.

10. Apparatus as claimed in claim 9, characterized in that the part of the rotational body forming one side of the gap constitutes the curved surface of the truncated cone, and in that the measurement section gap lies in a plane perpendicular to the rotational axis of the rotational body.

* * * * *